United States Patent [19]

O'Brien et al.

[11] Patent Number: 4,474,056

[45] Date of Patent: Oct. 2, 1984

[54] ERYTHROCYTE SETTLING RATE METER

[75] Inventors: Robert N. O'Brien; Philip M. McOrmond; Martin B. Hocking; Kenneth R. Thornton, all of Victoria, Canada

[73] Assignee: University of Victoria, Victoria, Canada

[21] Appl. No.: 389,252

[22] Filed: Jun. 17, 1982

[30] Foreign Application Priority Data

Aug. 18, 1981 [CA] Canada .................................. 384115

[51] Int. Cl.³ ........................................... G01N 15/04
[52] U.S. Cl. ................................................. 73/61.4
[58] Field of Search .................... 73/61.4; 346/33 ME

[56] References Cited

U.S. PATENT DOCUMENTS

| | | | |
|---|---|---|---|
| 2,379,158 | 2/1943 | Kalischer | 73/61.4 X |
| 3,952,579 | 4/1976 | Nakajima | 346/33 ME X |
| 4,118,974 | 10/1978 | Nozaki et al. | 73/61.4 |
| 4,182,161 | 1/1980 | Greenfield | 73/61.4 |

FOREIGN PATENT DOCUMENTS

| | | | |
|---|---|---|---|
| 916128 | 8/1954 | Fed. Rep. of Germany | 73/61.4 |
| 2341403 | 2/1975 | Fed. Rep. of Germany | 73/61.4 |
| 2631291 | 1/1978 | Fed. Rep. of Germany | 73/61.4 |

Primary Examiner—Gerald Goldberg
Assistant Examiner—Joseph W. Roskos
Attorney, Agent, or Firm—Weinstein & Sutton

[57] ABSTRACT

A novel meter is provided for measuring erythrocyte settling rates. It includes (a) a base supporting rack adapted to hold an array of tubes at an optimum settling angle and at least one tube adapted to contain blood samples, the tube including a window of predetermined length at the upper end thereof, the window permitting passage of ambient light therethrough. A timer is provided which is actuated by the passage of ambient light through the window when the tube contains blood, to determine the erythrocyte settling rate. This timing is achieved by signalling that a preset period of time has elapsed between when a minimum amount of light passes through the window, indicative of the presence of erythrocytes in the area of the window, and when a maximum amount of light passes through the window, indicative of the substantial absence of erythrocytes in the area of the window. By this invention, a blood test may be done in 5 to 15 minutes. A doctor (or probably his nurse) can perform the test while continuing the examination of the patient and have the results in time for diagnosis.

14 Claims, 3 Drawing Figures

ERYTHROCYTE SETTLING RATE METER

BACKGROUND OF THE INVENTION (i) Field of the Invention

This invention relates to a meter for measuring erythrocyte settling rates.

(ii) Description of the Prior Art

Measurement of erythrocyte settling rates, usually described as a blood test, is one of the most common medical tests made. When pathogens are present, extra antibodies are secreted and carried in the blood. These are mainly proteins and they cause clumping of red blood cells into rouleaux which are larger than normal and hence settle faster. A blood test shows this, but such test, as presently operated, usually requires two hours for reliable results. In one standard form of blood test, a specific amount of anticoagulant must be used (to prevent clotting during the test) and, to ensure good mixing, a few minutes of shaking of the blood sample is required. Then a sample must be placed in a vertical rack, a timer set and the rate of sedimentation (3 mm/hour for healthy humans) observed for one to two hours. Usually the operation is done in a hospital or clinical laboratory. This generally means that with transportation delays, the results may not be known until the next day.

Other proposals have been made in analogous fields to determine settling rates for solids, or cloud points of liquids. In Canadian Pat. No. 715,290 issued Oct. 10, 1965 to P. G. Holdbourne, a method is provided for continuously monitoring the cloud point or the pour point of hydrocarbon oil, involving the use of a beam of light which is directed through the oil onto a reflecting surface. The temperature of the oil is measured when the intensity of the beam of light reflected from the reflecting surface decreases a predetermined amount.

Canadian Pat. No. 912,849 issued Aug. 10, 1972 to P. Cahour at al provides a device for controlling the rate of settlement of a solid in suspension in a liquid involving the use of a settlement cell comprising a vertical, transparent glass column, and a projector for projecting a horizontal beam of light through the column to be picked up by a photoelectric cell which can produce a signal that detects the precise moment when the settling face moves past that level.

U.S. Pat. No. 2,379,158 issued June 26, 1945 to P. R. Kallscher et al provides a technique for the determination of the characteristics of the particles in a powdered material using an apparatus including a vertically disposed settling column, a light source and a light sensitive device disposed about the settling column to indicate the relative light transmission through a cross-sectional portion of the column, the column being transparent at this point. The light source and light sensitive device are disposed at a sufficient distance from the admission end of the column so that the admitted particles of the powdered material, under the influence of settling forces, undergo a relative gradation resulting in closely similar sized particles being present in any cross-sectional volume of dispersing medium in the settling column when the particles settle past the portion through which light from the light source passes.

U.S. Pat. No. 2,514,260 issued July 4, 1950 to M. S. Rosen provides apparatus for determining the rate of sedimentation of the solid particles in a fluid menstruum, e.g., the erythrocyte sedimentation rate of any blood or fluid containing blood. The apparatus includes a container comprising two parallel circular discs connected at their peripheries by a cylindrical band. The container, when filled with blood, must be maintained vertical. A circular opening is located at one point on the band and a short tube is connected with the opening to facilitate filling of the space between the discs and the band. One face of the disc has indices thereon, to permit reading of volumes of sediment settling within the container. U.S. Pat. No. 2,528,704 issued Nov. 7, 1950 to P. M. Neuda provides apparatus for determination of the settling rate of erythrocytes. The erychrocyte settling container is of predetermined triangular vertical section which gradually widens from its top to the bottom. The container is disposed so that there is a vertical orientation go that a wide zone of separation of the fluid-solid mixture is provided at the bottom while, simultaneously, both a quick transfer of the plasma through narrowing spaces toward the surface and a subsequent speed sedimentation of the erythrocytes through spaces widening towards the bottom is secured.

U.S. Pat. No. 2,741,913 issued Apr. 17, 1956 to N. Dovau relates to improvements in racks for holding ungraduated sedimentation tubes against a graduated background. The patented rack is for holding sedimentation tubes beside graduated scales and comprises a body block member having bottom feet and a central portion supported by and bridging such feet, a front face and a plurality of spaced vertically oriented sedimentation tube openings adjacent the front face, a plurality of spaced graduated scales on the front face adjacent the openings, and a plurality of spring clips secured to the body block member and disposed in the openings removably to hold sedimentation tubes therein.

U.S. Pat. No. 3,009,352 issued Nov. 21, 1961 to P. M. Neuda provides an improvement in the Neuda triangle of U.S. Pat. No. 2,528,704. The new triangular container is a triangularly shaped flat container, the sides of the triangle being equilateral, with a top aperture, a V-shaped neck outside the triangle, with each side of the V being exactly parallel to the side of the triangle opposite thereof, and a precise scale, on the outside of the triangular container calibrated in desired units.

U.S. Pat. No. 3,411,352 issued Apr. 29, 1969 to L. A. Hughes provides a colorimeter which includes a plurality of photoelectric cells, each having associated with it a light filter which removes all except the particular monochromatic band of light to which the photoelectric cell is primarily responsive and where its peak response is located. Thus, a different cell is used for each colour of light. A receptacle receives a colorimeter cuvette containing a specimen, a spring in the cuvette urging it against one side thereof. At one side of the receptacle is an electric lamp as a light source and on the diametrically opposite side, against which the cuvette is urged, are a plurality of vertically displaced photoelectric cells. Each cell has maximum sensitivity to a different monochromatic light and has associated with it a filter for transmitting to the cell that monochromatic light to which its cell has maximum sensitivity. An electric circuit includes the lamp, switch means for placing each cell in the circuit, only one at any time, a bridge circuit responsive to the current of the cell then in the circuit, and an electrical heater which operates na incubator having a plurality of cuvette receptacles. A plurality of interchangeable meters, each relevant to one particular test and calibrated for direct reading in that test in conjunction with one cell and each insertable into and removable from the electric circuit is supplied, but only one is used at a time across the bridge circuit for measuring light transmissivity of the specimen as expressed by the current passing through the photoelectric cell then in the electric circuit. Some of these meters have an actuator and some do not, the actuator, when present, throwing the switch means to place a different cell in the electric circuit.

U.S. Pat. No. 3,812,966 issued May 28, 1979 to W. A. Beach et al provides a determination of the settling rate of particulate matter by passing a mixture of the fluid and the particulate matter through an inclined tube at a known flow rate within the laminar flow range. Lights are positioned on one side of the inclined tube, and photocells are positioned on the other side. The signals generated thereby may be used to control the operation of a separator.

U.S. Pat. No. 4,027,971 patented June 7, 1977 by P. Kolman et al provides an analytical apparatus for counting the quantity of blood cells, suspended in a predetermined quantity of blood fraction. White light, which is directly transmitted through a predetermined volume of the blood, is filtered through a light filter, and light of the selected optical wavelength is passed through.

U.S. Pat. No. 4,187,462 patented Feb. 5, 1980 by R. Haker et al provides a device for determining the blood sedimentation rate in a substantially vertical test tube. The electrical or magnetic property of a given volume of liquid, which is changed by the settling of the erythrocytes in the test tube is measured as a function of time, by electrical means.

German Offenlegungsschrift No. 2,324,015 published Nov. 28, 1974 provides a system for measuring the settling speed of erythrocytes in blood by resonant frequency measurement.

Finally, German Pat. No. 916,128 dated July 8, 1949 of J. Reppisch provides a blood test machine in which tubes containing blood are held in an inclined position, and in which the settling rate is estimated visually.

SUMMARY OF THE INVENTION (i) Aims of the Invention

In spite of these patents, there is still a need for an improved erythrocyte settling meter. An object, therefore, of this invention is the provision of an improved erythrocyte settling meter in which the test may be determined rapidly.

Another object of this invention is to provide such meter in the form of a simple hand-held stop-watch timed device, a partially automated device suitable to a doctor's office or a fully automated device for hospitals and clinics.

(ii) Statement of Invention

This invention therefore provides an erythrocyte settling meter comprising: (a) a rack adapted to hold an array of tubes at an optimum settling angle; (b) at least one tube adapted to contain blood samples, the tube including a window of predetermined length at the upper end thereof, the window permitting passage of ambient light therethrough; and (c) timing means actuated by the passage of ambient light through the window when the tube contains blood, to determine the erythrocyte settling rate by signalling that a preset period of time has elapsed between when when a minimum amount of light passes through the window, indicative of the presence of erythrocytes in the area of the window, and when a maximum amount of light passes through the window, indicative of the substantial absence of erythrocytes in the area of the window.

(iii) Other Features of the Invention

By one feature thereof, the angle is from 20° to 70° from the horizontal, preferably 60° from the vertical.

By another feature, the window is 1 cm in length and the remain-of the tube is coloured so that ambient light may not shine therethrough.

By a further feature, a plurality, e.g., more or less than ten such tubes are provided, the tubes having means of clearly differentiating or marking one tube from another, e.g., by making each tube of a different colour.

By a further feature, the means (c) comprises an electrical circuit including a photocell to generate an electric current to commence the timing when such minimum amount of light passes through the window and impinges on the photocell.

By another feature, the meter includes a clamp and pressure switch on the upper portion of the rack, the switch being closed by the clamping of the tube containing blood onto the rack to complete an electrical circuit to the photocell, thereby to commence the timing when the tube containing the blood is clamped into position.

By another feature, the electrical circuit means including an amplifier, a diode, an electrically operated numeric display, and a thermomechanical switch which initially does not complete a circuit to the electrically operated numeric display when the pressure switch is closed but which completes a circuit to the electrically operated numeric display after a lapse of time no longer than the preset period of time, thereby to signal lapse of such time on the electrically powered numeric display.

By a further feature, the meter includes a second thermomechanical switch which initially does not complete a circuit to a second electrically operated numeric display but which after the lapse of a further preset period of time completes a circuit to the second electrically operated numeric display, thereby to signal that such additional preset period of time has elapsed on the second electrically operated numeric display.

By yet another feature, the meter includes a bubble level in the base of the rack to assure that the base is level.

(iv) Generalized Description of the Invention

The invention in one of its embodiments consists of an inclined rack on which a blood test sample tube is placed. The rack has in its base a bubble level to allow the base to be levelled. The inclined rack is fixed at 60° from the vertical. Depending on the model, up to ten tubes may be used on the inclined rack at once.

The rack is provided with means to enable the settling rate to be determined. It may be a simple visual means, by the operator or person who carries out the test whereby the time it takes the blood sample to go from a turbid condition at the window to a clear condition at the window can be timed by a stop watch.

It can be by means of a recorder to set up the initial and normal times coupled with an indication of the time at which there is a clear condition at the window, the indication being also determined by the recorder.

Finally, a series of numeric indicators, i.e., LED or other electrically activated lighted numbers, can be lit automatically as the condition at the window clears.

BRIEF DESCRIPTION OF THE DRAWINGS

In the accompanying drawings.

DESCRIPTION OF PREFERRED EMBODIMENTS

Figure 1:
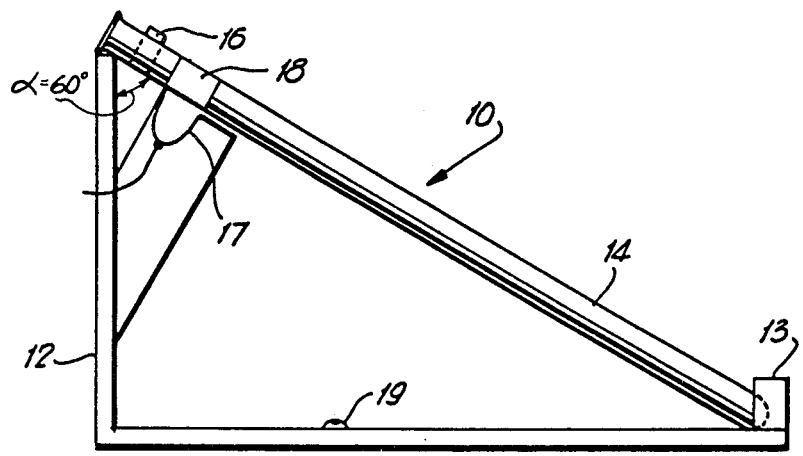
FIG. 1 is a side elevational view of a simple erythrocyte settling rate meter.
Figure 2:
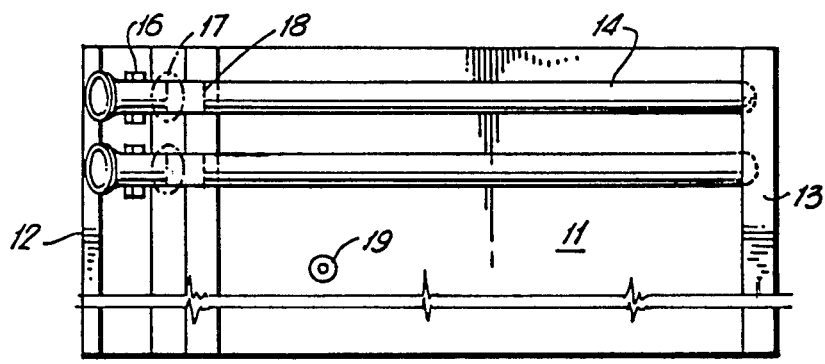
FIG. 2 is a top plan view thereof.

The embodiment of the invention shown consists of a rack 10 including a base 11, a rear upright 12 and a forward foot 13. Preferably, the rack is made from polycarbonate or polymethylmethacrylate sheet. The height of rear upright 12 is such that blood sample tubes 14 are inclined at an angle ($\alpha$) of 60°.

Near the head 15 of the rack is a clamp and pressure switch 16 coupled to a photocell arrangement 17, to pick up ambient light shining through window 18. A plurality of the blood sample tubes 14 are fixed to the rack by means of the like plurality of clamps and pressure switches 16. The base 11 includes a bubble level 19.

The blood sample tubes 14 have a filling mark. It is imperative that the tube be filled to that mark for good results. About 1 cm of the tube below the mark is clear to provide the window 18 and the rest of the tube is coloured. It is preferred that the tubes have ten different colours.

Figure 3:
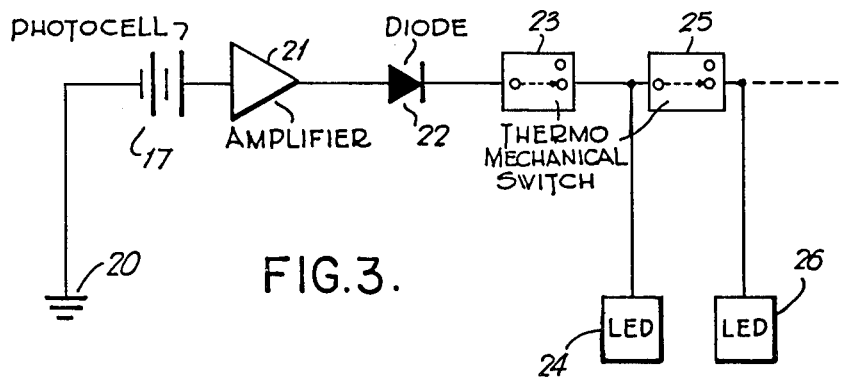
FIG. 3 is a simple schematic electrical circuit thereof.

As seen in FIG. 3, which is one embodiment of a circuit arrangement, the photocell 17 has one terminal grounded at 20 and has its other terminal connected to an amplifier 21. The output of the amplifier 21 passes through a diode 22 to a first thermomechanical switch (indicated schematically as block 23) which, when it reaches a predetermined temperature after the passage of a maximum period of time, lights the first LED display 24. The circuit also includes to a second thermomechanical switch (indicated schematically as block 25), which, when it reaches a predetermined higher temperature than switch 23 after the passage of a longer period of time than the maximum period of time for switch 23 lights second LED display 26. This LED 24 lights up after maximum elapsed time of 5 minutes, while LED lights up after a minimum elapsed time of more than 5 minutes.

A third thermomechanical switch/LED display (not shown) may also be provided in the circuit.

OPERATION OF PREFERRED EMBODIMENT

In operation, clamping the blood sample tubes 14 into the rack 10 opens the circuit to the LED displays (24, 26) from the photocell. As the erythrocytes settle, the clear plasma allows the ambient light shining through window 18 to activate the photocell voltage. This is amplified at amplifier 21, passes through the diode 22 and begins to warm the first switch 23. Thermomechanical switch 23 is of a conventional construction well-known in the art. It has an internal construction including resistive elements enabling it to complete the circuit to the photocell 17 and thus to be heated. Thermomechanical switch 23, after reaching a preset temperature, dependent on the magnitude of the current originating at the photocell 17, which, in turn is dependent on the amount of light impinging on the photocell 17, completes a circuit to a first LED display 24, thereby lighting display 24. The maximum time required to complete the circuit to the first LED 24 is when the current is at a minimum, which, in one embodiment is five minutes. This is indicative of a minimum amount of light impinging on the photocell when erythrocytes are present at the area of the window. The minimum time required to complete the circuit to the first LED 24 is when the current is at a maximum, which would be less than five minutes. This is indicative of a maximum amount of light impinging on the photocell 17 when substantially no erythrocytes are present at the area of the window. The circuit including photocell 17, amplifier 21, diode 22 and first thermomechanical switch 23 also includes a second thermomechanical switch shown schematically at 25. Thermomechanical switch 25 also has an internal construction, e.g. resistive elements enabling it to complete the circuit to the photocell 17 and thus to be heated. Thermomechanical switch 25 after reaching a preset higher temperature than that of first thermomechanical switch 23, and which is dependent on the magnitude of the current originating at the photocell 17, which, in turn is dependent on the amount of light impinging on the photocell 17, completes a circuit to the second LED display 26, thereby lighting display 26. This circuit supplies insufficient current to warm the thermomechanical switch 23 sufficiently to light the LED display 24 if sedimentation is not fast enough. As described above, whether LED 24 is lit or not, the photocell current passes through the second thermomechanical switch 25, which after the lapse of an additional period of time, as described above heats up sufficiently after the lapse of an addition period of time, lights another LED and so to the third (not shown). If the instrument is started and left for a long time, all three LED's will be lit, but if looked at in five minutes when, as described above, only LED 24 will be lit, the blood can be judged normal or abnormal.

The sedimentation rate of the erythrocytes (blood cells) is very different in the inclined position compared to the ordinary vertical settling position.

EXAMPLE

In the standard vertical test, it requires 60 minutes to settle 3 mm for normal blood and abnormal-to-normal ratios can be read up to 18 with settled distances of up to 55 mm. In the inclined settler, the normal blood settled 4 mm in ten minutes and ratios of abnormal-to-normal reached 19 and settled distances of 77 mm. In five minutes only, very often useful differentiation is possible (see tables below).

| Standard E.S.R. test | | Inclined E.S R. test | |
| --- | --- | --- | --- |
| Settled distance, mm (60 min) | Ratio, abnormal/ slow normal | Settled distance, mm (10 min) | Ratio, abnormal/ slow normal |
| 3 | 1.0 | 4 | 1.0 |
| 4 | 1.3 | 14 | 3.5 |
| 6 | 2.0 | 22 | 5.5 |
| 10 | 3.3 | 26 | 6.5 |
| 15 | 5.0 | 34 | 8.5 |
| 22 | 7.3 | 38 | 9.5 |
| 23 | 7.7 | 39 | 9.8 |
| 27 | 9.0 | 60 | 15.0 |
| 46 | 15.3 | 72 | 18.0 |
| 55 | 18.3 | 77 | 19.3 |

| Standard E.S.R. test | | | Inclined E.S.R. test | | | |
| --- | --- | --- | --- | --- | --- | --- |
| Settled distance, mm (60 min) | Ratio, abnormal/ 4 mm normal | Ratio, abnormal/ 3 mm normal | Settled distance, mm (5 min) | Ratio, abnormal/ 4 mm normal | Settled distance, mm (15 min) | Ratio, abnormal/ 3 mm normal |
| 3 | — | 1.0 | 0 | — | 24 | 1.0 |
| 4 | 1.0 | 1.3 | 0.5 | 1 | 28 | 1.2 |
| 6 | 1.5 | 2.0 | 3 | 6 | 38 | 1.6 |
| 10 | 2.5 | 3.3 | 4 | 8 | 42 | 1.8 |
| 15 | 3.8 | 5.0 | 10 | 20 | 59 | 2.5 |
| 22 | 5.5 | 7.3 | 9 | 18 | 56 | 2.3 |
| 23 | 5.8 | 7.7 | 9 | 18 | 55 | 2.3 |
| 27 | 6.8 | 9.0 | 6 | 12 | 88 | 3.7 |
| 46 | 11.5 | 15.3 | 19 | 38 | 95 | 4.0 |
| 55 | 13.8 | 18.3 | 23 | 46 | 98 | 4.1 |

DESCRIPTION OF OTHER EMBODIMENTS

While not shown, other variants of this invention are possible. For a so-called clinical model, a simple recorder is provided to draw a line at the start (tube clipped on, switch closed) on its time base beginning at a predetermined point on chart paper numbered with the numbers of the tube in the rack (say, 1 to 10). When the signal from the appropriate photocell has not increased in one minute, the recorder will draw another line. This time will then be compared against a normal time.

The simplest model will have ten positions on the rack and ten sample tubes. Ten tubes can be filled, kept vertical, then shaken and placed in the rack and timed by stop-watch or wall clock with a second hand.

SUMMARY

The present invention will allow a determination to be made in 5 to 15 minutes. A doctor (or probably his nurse) can perform the test while continuing the examination of the patient and have the results in time for diagnosis.

The system would also be of great assistance during natural disasters. For example, during flooding, distressed people will appear who are suffering from no disease, just exposure, hunger, anxiety, etc., but there will be those who have drunk contaminated water and are suffering from water-borne diseases. Those with a disease can, with the aid of the erythrocyte settling meter of aspects of this invention, be quickly separated.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A meter for measuring erythrocyte settling rates, comprising:
   (a) a rack adapted to hold an array of tubes at an optimum settling angle;
   (b) at least one tube adapted to contain blood samples, said tube including a window of predetermined length at the upper end thereof, the window permitting passage of ambient light therethrough;
   (c) timing means actuated by the passage of ambient light through said window when said tube contains blood, to determine the erythrocyte settling rate by signalling that a preset period of time has elapsed between when a minimum amount of light passes through said window, indicative of the presence of erythrocytes in the area of said window, and when a maximum amount of light passes through said window, indicative of the substantial absence of erythrocytes in the area of said window.

2. The meter of claim 1 wherein said angle is from 20° to 70° to the horizontal.

3. The meter of claim 1 wherein said angle is 60° to the horizontal.

4. The meter of claim 1 wherein said window is of significant length and wherein the remainder of the tube is coloured so that ambient light is prevented from passing therethrough.

5. The meter of claim 4 wherein said window is 1 cm in length.

6. The meter of claim 4 wherein a plurality of such tubes are provided, said tubes having means of clearly differentiating or marking one tube from another.

7. The meter of claim 6 wherein each tube is of different colour.

8. The meter of claim 6 wherein ten such tubes are provided.

9. The meter of claim 7 wherein ten such tubes are provided.

10. The meter of claim 1 wherein said means (c) comprises an electrical circuit including a photocell to generate an electric current to commence said timing when said minimum amount of light passes through said window and impinges on said photocell.

11. The meter of claim 10 including a clamp and pressure switch on the upper portion of said rack said switch being closed by the clamping of said tube containing blood onto said rack to complete an electrical circuit to said photocell, thereby to commence said timing when said tube containing said blood is clamped into position.

12. The meter of claim 11 wherein said electrical circuit includes an amplifier, a diode, an electrically operated numeric display, and a thermomechanical switch which initially does not complete a circuit to said electrically operated numeric display when said pressure switch is closed but which completes a circuit to said electrically operated numeric display after a lapse of time no longer than said preset period of time, thereby to signal passage of said preset period of time on said electrically operated numeric display.

13. The meter of claim 12 including a second thermomechanical switch which initially does not complete a circuit to a second electrically operated numeric display but which, after the lapse of a further preset period of time, completes a circuit to said second electrically operated numeric display, thereby to signal that said additional preset period of time has elapsed on said second electrically operated numeric display.

14. The meter of claim 1 including a bubble level in the base of the rack to assure that the base is level.

* * * * *

UNITED STATES PATENT AND TRADEMARK OFFICE
CERTIFICATE OF CORRECTION

PATENT NO. : 4,474,056
DATED : October 2, 1984
INVENTOR(S) : Robert N. O'Brien, et al It is certified that error appears in the above—identified patent and that said Letters Patent is hereby corrected as shown below:

Column 1, line 39, change "at al" to --et al--.

Column 2, line 15, change "go" to --so--.

Signed and Sealed this

Ninth Day of April 1985

[SEAL]

Attest:

DONALD J. QUIGG

Attesting Officer     Acting Commissioner of Patents and Trademarks